United States Patent [19]

Scholz

[11] Patent Number: 5,466,606
[45] Date of Patent: Nov. 14, 1995

[54] USE OF N-METHYLFORMAMIDE AS SOLVENT FOR THE KARL FISCHER TITRATION

[75] Inventor: Eugen Scholz, Garbsen, Germany

[73] Assignee: Riedel-De Haen Aktiengesellschaft, Seelze, Germany

[21] Appl. No.: 293,312

[22] Filed: Aug. 22, 1994

[30] Foreign Application Priority Data

Aug. 31, 1993 [DE] Germany ............... 43 29 287.9

[51] Int. Cl.$^6$ .................................. G01N 33/18
[52] U.S. Cl. ............... 436/42; 436/39; 436/171; 422/61; 422/82.01; 252/408.1; 204/153.23; 204/405
[58] Field of Search ............... 436/42, 39, 171; 252/408.1; 422/61, 82.01; 204/153.23, 405

[56] References Cited

U.S. PATENT DOCUMENTS

| | | | |
|---|---|---|---|
| 4,354,853 | 10/1982 | Dahms | 436/42 |
| 4,619,900 | 10/1986 | Schulz | 436/42 |
| 4,725,552 | 2/1988 | Dahms | 436/42 |
| 4,851,352 | 7/1989 | Fischer et al. | 436/42 |
| 4,874,709 | 10/1989 | Fischer et al. | 436/42 |
| 5,340,541 | 8/1994 | Jackson et al. | 422/75 |

FOREIGN PATENT DOCUMENTS

| | | |
|---|---|---|
| 0135098 | 3/1985 | European Pat. Off. . |
| 0206017 | 12/1986 | European Pat. Off. . |
| 0299310 | 1/1989 | European Pat. Off. . |

OTHER PUBLICATIONS

Journal of Analytical Chemistyr of the USSR, "A New Electrolyte for the Coulometric Determination of Water", vol. 35, No. 11, Part 2 (Nov. 1980).

Analytical Chemistry, "Moisture Determination Using Karl Fischer Titrations", 63, No. 10, (May 15, 1990).

Analytica Chimica Acta, vol. 239, (1990), pp. 283–290.

*Primary Examiner*—Robert J. Warden
*Assistant Examiner*—N. Bhat
*Attorney, Agent, or Firm*—Connolly & Hutz

[57] ABSTRACT

The invention relates to the use of N-methylformamide as solvent in the determination of water by the Karl Fischer method.

12 Claims, No Drawings

USE OF N-METHYLFORMAMIDE AS SOLVENT FOR THE KARL FISCHER TITRATION

The Karl Fischer titration for determination of water is one of the standard methods of analytical chemistry and is comprehensively described in the literature. It is carried out in two basic forms, namely as a volumetric titration and as a coulometric titration.

There are two variants of the volumetric titration. In most cases, the titration is carried out using a single-component reagent, i.e. using a reagent solution which contains sulphur dioxide, one or more bases, iodine and a suitable solvent which nowadays is preferably 2-methoxyethanol. To carry out such a titration, the sample is dissolved in a solvent and then titrated with the KF single-component reagent. The preferred solvent is methanol.

A variant of the volumetric titration is the use of a two-component reagent comprising a solvent component which is sulphur dioxide, one or more bases and methanol as solvent and a titrant component which is a solution of iodine in a suitable solvent such as methanol or xylene. The solvent component is used as solvent for the sample. Titration is carried out using the titrant component.

In the coulometric determination, the iodine is generated by anodic oxidation and then reacts with the other components of the KF system in a known manner. In the preferred form of coulometry, the coulometric cell comprises a large anode space in which the KF reaction occurs and a small cathode space in which an adequate cathode reaction occurs. The reagent for the anode space normally comprises sulphur dioxide, one or more bases, a soluble iodide and an alcoholic solvent, preferably methanol. The reagent solution has to have a minimum conductivity value so that the current required for the reaction can flow. For this reason, conductive salts are occasionally added. The reagent for the cathode space has to have an adequate conductivity and make possible a cathode reaction. For this purpose, KF reagents of similar composition are predominantly used.

A variant of coulometry is the use of the diaphragmless cell so that only one reagent has to be used. Suitable reagent solutions for this purpose correspond in principle to the composition which has been designated above as reagent for the anode space.

The basic forms of the Karl Fischer titration are modified in practice if this is required by the substance to be analysed. For the analysis of fat-like substances, the reagent solutions used are admixed with chloroform, xylene or long-chain alcohols (EP 0 299 310) to improve the solvent capability for these substances.

If the customarily used alcohols, preferably methanol, react with the samples to be analysed, e.g. with aldehydes or ketones, preference is given to substituted alcohols (EP 0 135 098).

There are limits to the addition of other solvents. Long-chain or substituted alcohols do make possible the analysis of hydrocarbons or of ketones, but at the same time interfere with the course of the Karl Fischer titration. In the coulometric reagents, they reduce the conductivity value of the Karl Fischer solution to such an extent that the apparatus are no longer capable of functioning. In the volumetric determination, they shift the end-point indication when present in relatively high concentration, so that the apparatus overtitrate and falsify the results. It is generally recognized that a Karl Fischer reagent contains an alcohol, since otherwise the stoichiometric course is changed (Scholz, Karl-Fischer-Titration, Springer-Verlag 1984, page 5).

Surprisingly, it has now been found that using N-methylformamide as solvent it is possible to prepare Karl Fischer reagents which react in the same way as the alcohol-containing reagents. They show the same stoichiometric reaction course, i.e. the ratio $H_2O: I_2$ is 1:1, as in alcoholic solutions. In addition, they show a series of additional advantages. N-Methylformamide is a good solvent for polar compounds and gives high conductivity values with dissolved salts. Thus, Karl Fischer reagents based on N-methylformamide are outstandingly suitable for the coulometric determination of water. In the volumetric titration, they give, for the same reason, a sharp end point and thus accurate results.

The secondary reaction occurring in the case of alcohols, e.g. ketal formation with ketones or the reaction with silanol groups, cannot occur in the case of N-methylformamide, so that this solvent and the reagents prepared therewith are outstandingly suitable for the determination of water in ketones.

Comparable solvents such as formamide and N,N-dimethylformamide have been tested and proved unsuitable. Formamide gives a secondary reaction which causes a rapid decomposition of single-component reagents and, in the case of reagents prepared therefrom, prevents a stable end point (Wünsch, Schöffski, Analytica Chimica Acta 239 (1990) 283–290). Dimethylformamide gives reagents in which the stoichiometry is shifted. The titer of these reagents depends on the solvent which is used for the samples (Scholz, page 5).

N-Methylformamide can be used in all forms of the Karl Fischer titration, in the volumetric titration using a single-component reagent or using a two-component reagent and in the coulometric titration in the two-chamber and single-chamber cell. All customary Karl Fischer bases such as, for example, pyridine, imidazole and aminoalcohols can be used. Examples of such reagents are given below.

N-Methylformamide can also be used in admixture with other solvents such as chloroform, xylene, alcohols or alcoholic reagents, so that the solvent combination of N-methylformamide with alcohols and/or other solvents can be matched to the requirements of the sample.

Example 1

140 g of imidazole are dissolved in 1000 g of N-methylformamide. 60 g of sulphur dioxide are then passed in while cooling so that the temperature does not exceed 30° C. Finally, 60 g of iodine are added. The solution is allowed to stand overnight. It is then standardized.

Example 2

The solvent component of a two-component reagent is prepared by dissolving 160 g of pyridine in 1000 g of N-methylformamide. Subsequently, 64 g of $SO_2$ are passed in, with the temperature being kept below 30° C. by means of cooling.

Example 3

The titrant component of a two-component reagent is prepared by dissolving 60 g of iodine in 1000 g of N-methylformamide.

Example 4

A coulometric reagent is prepared by dissolving 105 g of imidazole in 1000 g of N-methylformamide. 64 g of sulphur dioxide are passed in while cooling, and finally 20 g of imidazole hydroiodide are added. The reagent thus prepared can be used in the anode space of the coulometric two-chamber cell or as universal electrolyte in the single-chamber cell.

Example 5

For use in the cathode space, 210 g of diethanolamine hydrochloride are dissolved in 1000 g of N-methylformamide.

Example 6

105 g of diethanolamine and 60 g of imidazole are dissolved in 500 g of N-methylformamide and 500 ml of methanol. 94 g of sulphur dioxide are then passed in while cooling. Subsequently, 40 g of sodium iodide are added. This reagent can be used as solvent component for a two-component reagent or as coulometric reagent.

USE EXAMPLES

The Use Examples are based on the nowadays customary forms of the Karl Fischer titration. In volumetric analysis, the solvent (in the case of the two-component reagent, the solvent component) is placed in a suitable titration vessel. The sample is then added and titrated with the Karl Fischer reagent (or the titrant component). Prior to the addition of the sample, the solvent can be titrated dry (dewatered) in a preliminary titration. The sample is then added and titrated in the same way.

In coulometry, the reagent is placed in the titration cell of commercial apparatus, with a two-chamber and single-chamber cell being usual. After switching on the apparatus, the reagents charged are automatically titrated dry. The sample is then added in accordance with the directions for the apparatus and is analysed.

Use Example 1

The volumetric titration cell is initially charged with methanol. The water-containing sample is added and titrated using a titrant in accordance with Example 1.

Use Example 2

The volumetric titration cell is initially charged with N-methylformamide. The water-containing sample is added and titrated using a titrant in accordance with Example 1.

Use Example 3

The volumetric titration cell is initially charged with N-methylformamide. The water-containing sample is added and titrated using a commercial Karl Fischer reagent in accordance with DAB 10.

Use Example 4

The volumetric titration cell is initially charged with the solvent component in accordance with Example 2. The water-containing sample is added and titrated using a titrant in accordance with Example 3.

Use Example 5

The volumetric titration cell is initially charged with the solvent component in accordance with Example 2. The water-containing sample is added and titrated using the titrant component in accordance with Example 3.

Use Example 6

The volumetric titration cell is initially charged with the solvent component in accordance with Example 2. The water-containing sample is added and titrated using a commercial titrant component (e.g. a solution of 65 g of iodine in methanol).

Use Example 7

The volumetric titration cell is initially charged with a commercial solvent component which comprises, for example, 120 g of pyridine and 60 g of sulphur dioxide dissolved in methanol. The water-containing sample is added and titrated using the titrant component in accordance with Example 3.

Use Example 8

The anode space of a coulometric cell, having two separate chambers, of a commercial Karl Fischer coulometer is charged with the reagent in accordance with Example 4. The cathode space is charged with the reagent in accordance with Example 5. Using these reagents, the water is determined in the appropriate manner.

Use Example 9

A coulometric cell, having only one chamber, of a commercial Karl Fischer coulometer is charged with the reagent in accordance with Example 6. Using this reagent, the water is determined in the appropriate manner.

I claim:

1. In a method for determining water content of a sample using the Karl Fischer reaction including the titration of a water containing sample with a Karl Fischer reagent comprising sulphur dioxide at least one Karl Fischer base; an iodide or iodine and a solvent wherein the improvement comprises the use of a solvent containing N-methylformamide.

2. A single component Karl Fischer reagent for the determination of water comprising sulphur dioxide; at least one Karl Fischer base; iodide, or iodine and a solvent containing N-methylformamide.

3. In a method for determining water content of a sample according to claim 1, using a two-component Karl Fischer reagent comprising a solvent component containing sulphur dioxide and at least one base selected from the group consisting of pyridine, imidazol and aminoalcohol, and a titrant component which is an iodine solution, wherein the solvent component contains N-methylformamide as the solvent.

4. In a method for determining water content of a sample according to claim 1, using a two-component Karl Fischer reagent comprising a solvent component containing sulphur dioxide and at least one base selected from the group consisting of pyridine, imidazol and aminoalcohol, and a titrant component which is an iodine solution, wherein titrant component contains N-methylformamide as the solvent.

5. In a coulometric determination of water in a two-chamber Karl Fischer cell, wherein the improvement comprises using an anode reagent containing sulphur dioxide, at least one base selected from the group consisting of pyridine, imidazol and aminoalcohol and a soluble iodide, wherein the node reagent contains N-methylformamide as a solvent.

6. In a coulometric determination of water in a two-chamber Karl Fischer cell, wherein the improvement comprises using, in the cathode space, a cathode reagent, an electrolyte containing one or more soluble conductive salts, wherein the cathode reagent contains N-methylformamide as a solvent.

7. In a coulometric determination of water in a single-chamber Karl Fischer cell wherein the improvement comprises using a reagent containing sulphur dioxide, at least one base selected from the group consisting of pyridine, imidazol and aminoalcohol, an iodide and N-methylformamide as a solvent.

8. The method according to claim 1, further comprising at least one additional solvent other than N-methylformamide.

9. The method according to claim 8, wherein the additional solvent is an alcohol or hydrocarbon.

10. The method according to claim 8, wherein the additional solvent is chloroform, xylene, alcohol or alcoholic reagents.

11. A two-component Karl Fischer reagent for the determination of water comprising:

1) a solvent component containing sulphur dioxide, at least one Karl Fischer base and a solvent, and 2) a titrant component containing iodine and a solvent, wherein the solvent of the solvent component or the solvent of the titrant component or the solvent of the solvent component and the solvent of the titrant component contain N-methylformamide.

12. In a method for determining the water content of a sample using the Karl Fischer reaction including the titration of a water containing sample with a single-component Karl Fischer reagent comprising sulphur dioxide, at least one Karl Fischer base, iodine and a solvent wherein the improvement comprises the use of N-methylformamide as the solvent for the water containing sample.

* * * * *